United States Patent [19]

Bregman et al.

[11] 4,080,958
[45] Mar. 28, 1978

[54] APPARATUS FOR AIDING AND IMPROVING THE BLOOD FLOW IN PATIENTS

[75] Inventors: David Bregman, New York, N.Y.; Bruce L. Hanson, Wayne, N.J.; Sidney Wolvek, Brooklyn, N.Y.

[73] Assignee: Datascope Corporation, Paramus, N.J.

[21] Appl. No.: 662,287

[22] Filed: Feb. 27, 1976

[51] Int. Cl.² .............................................. A61M 1/03
[52] U.S. Cl. ........................................ 128/1 D; 3/1.7; 417/205
[58] Field of Search ............... 128/1 D, DIG. 3, 273, 128/214 F; 3/1.7; 417/205, 244, 384; 23/258.5 R, 258.5 A, 258.5 B, 258.5 BH, 258.5 M, 258.5 MH

[56] References Cited

U.S. PATENT DOCUMENTS

| Re. 27,849 | 12/1973 | Wortman | 3/1.7 |
|---|---|---|---|
| 3,572,979 | 3/1971 | Morton | 128/DIG. 3 |
| 3,639,084 | 2/1972 | Goldhaber | 128/1 D X |
| 3,656,873 | 4/1972 | Schiff | 128/DIG. 3 |
| 3,727,612 | 4/1973 | Sayers et al. | 128/214 R |
| 3,783,453 | 1/1974 | Bolie | 128/1 D X |
| 3,818,934 | 6/1974 | Borsanyi | 137/568 |
| 3,857,382 | 12/1974 | Williams et al. | 128/1 D |
| 3,860,968 | 1/1975 | Shapiro | 417/384 X |
| 3,877,609 | 4/1975 | Cullis | 222/1 |
| 3,911,898 | 10/1975 | Leachman | 128/1 D |
| 3,955,557 | 5/1976 | Takagi | 128/1 D |

FOREIGN PATENT DOCUMENTS

| 1,187,568 | 9/1959 | France | 128/1 D |
|---|---|---|---|
| 1,395,826 | 3/1965 | France | 128/1 D |
| 1,542,889 | 9/1968 | France | 128/1 D |
| 2,215,929 | 1/1974 | France | 128/1 D |
| 2,426,317 | 12/1975 | Germany | 128/1 D |
| 1,160,433 | 8/1969 | United Kingdom | 128/1 D |

OTHER PUBLICATIONS

Cardiovascular Diseases, Bulletin of the Texas Heart Institute, vol. 2, No. 4, 1975, pp. 405-409.
Journal of Cardiovascular Surgery, vol. 17, No. 5, Sep.-Oct. 1976, pp. 398-407.

*Primary Examiner*—Robert W. Michell
*Assistant Examiner*—Michael H. Thaler
*Attorney, Agent, or Firm*—Kenyon & Kenyon, Reilly, Carr & Chapin

[57] ABSTRACT

Improved blood pumping apparatus is disclosed which includes a smooth avalvular deflatable section through which blood flows, said section mounted within a rigid avalvular airtight housing, gas being introduced and withdrawn from the housing by suitable control means, the action of the gas causing the blood chamber to inflate and deflate with consequent non-traumatic pulsatile ejection of blood from said chamber. The apparatus is simple, reliable, inexpensive and can aid the blood pumping function in many ways. For example, apparatus is disclosed to provide pulsatile flow to the blood being pumped by a heart-lung machine, or to provide pulsatile flow to the coronary arteries during coronary artery perfusion, or to be utilized as an arterio-venous fistula to decrease the afterload of the left ventricle and preserve the systemic diastolic pressure while increasing coronary perfusion. In addition, apparatus is disclosed which can, with slight modification, function as counterpulsation apparatus to, for example, support a patient's systemic circulation by left heart counterpulsation, or wean a patient off a heart-lung machine when the patient's heart has resumed beating, or support the right heart by pulmonary artery counterpulsation, or provide counterpulsation when other types of counterpulsation, such as intra-aortic balloon pump counterpulsation, are impractical.

15 Claims, 7 Drawing Figures

APPARATUS FOR AIDING AND IMPROVING THE BLOOD FLOW IN PATIENTS

BACKGROUND OF THE INVENTION

In many medical situations, it becomes necessary or desirable to aid the patient's blood flow. In some cases, such as certain types of open heart surgery, it is necessary for external means to completely take over the blood pumping function of the heart since the heart is incapable of doing so. In other cases, the heart is weak and external means are used to aid the heart in its blood pumping function. In still other situations, certain organs, including the heart itself, require blood flow which the body is incapable of providing and which therefore must be supplied or assisted by external means.

It has been recognized that in all situations of the type described, it is preferable to have the blood pumped in a pulsatile manner, similar to the pumping action of a normal heart. On the other hand, this pulsatile flow must be provided with as little trauma to the blood as possible, since if the blood is subjected to high shear forces, it undergoes considerable damage. Such shear forces are encountered in certain types of pumps, such as roller pumps, which pump the blood by squeezing a plastic tubing containing the blood. Also any device containing valves is likely to damage the blood through the opening and closing of the valves. Therefore, during the past several years, attempts have been made to develop a system that will circulate the blood in a pulsatile manner and will, at the same time, not subject the blood to undue trauma. Tube-pumps, piston-pumps, diaphragm-pumps, sac pumps, peristaltic or finger pumps, and roller pumps have all been tried. They have all proved inadequate — the tube, diaphragm, piston and sac type pumps paying the price for pulsatile flow in increased blood trauma (hemolysis) caused by their valves and shear forces; the finger and roller pumps limiting operative time by the blood trauma induced by the nature of their occlusive action. The roller pump, notwithstanding its limitations, has become the standard pump used as the present day arterial perfusion pump, coronary perfusion pump, and venous and suction pump. Surgical procedure, such as cardio-pulmonary bypass, as it is understood at present, is therefore limited both in time and efficacy. The operative time is limited by the trauma induced to the blood by the occlusive pumping action and the efficacy by the lack of pulsatile flow.

SUMMARY OF THE INVENTION

The present invention solves the above-mentioned problems by providing a device which is capable of providing a pulsatile blood flow with the introduction of little or no additional trauma to the blood. The device is used in connection with presently known pumping systems to perform a variety of functions as more fully described hereinafter. The device may be inserted into the blood flow circuitry of such systems without the need for additional surgery to the patient, and in some cases may be used in place of present systems in a manner which involves less radical surgical procedures than those required for use of present systems.

The apparatus of the present invention to be utilized in combination with, or in some cases, in place of, existing systems, is in the form of a flexible, double-ended, balloon-like member through which the blood passes on its way to the patient. The device is constructed so that the blood comes into contact with no surface other than the smooth, unbroken surface of the balloon-like member and is completely free of valves which might traumatize the blood. This balloon or tubular member is constructed of a blood compatible, extremely flexible plastic having a very thin wall thickness. It collapses easily and throughout its entire length thus minimizing or eliminating any damage to the blood that passes through it. The tubular member is contained within a rigid housing of suitable transparent plastic. The housing terminates in ends which can be connected into existing blood pumping circuitry. Its overall cross section is not greatly larger than the pump tubings to which it is attached. It can be sterilized separately or pre-assembled to the other components of existing blood pumping circuitry. Air or some other suitable gas is pumped into the space between the rigid housing and the balloon via a suitable fitting, collapsing the balloon and forcing it to eject its bolus of blood into the circulatory system. The activating air or gas may be pumped, valved, regulated and timed by any suitable control means to coordinate with physiological needs of the patient or organ.

This device can be used with presently available blood pumping systems, such as a conventional heart-lung machine, to convert the non-pulsatile pressure waves delivered by the roller pump section of such systems into pulsatile pressure waves. Experiments have shown pulse pressure excursions of great magnitude and extremely large pulsations in the aortic flow rate with the apparatus of the present invention being used in combination with a heart-lung machine. The device can be inserted into the heart-lung circuitry to act in series with the roller pump to provide the aforementioned pulsatile waveform or it can be used to counterpulse a poorly functioning heart before cardio-pulmonary bypass support, or, for counterpulsation of a beating heart during that interval when the heart may not yet be able to maintain systemic pressures by itself. These various options may be taken without any additional surgery or implantation to the patient, beyond that needed for use of the heart-lung circuitry itself. Because of the device's small size and light weight it can be inserted into the system very close to the patient's aorta where experience has proven counterpulsation to be the most efficient. The device can be clamped in a variety of manners to the operating table or to the ether screen at the head of the table. In either position it can be under the constant observation of the surgeon and his assistant.

In addition, it has become common practice to perfuse the coronary arteries when the heart is stopped for aortic valve surgery for a reasonably long period of time. This is usually accomplished by the action of two smaller roller pumps on a heart-lung machine. Each pump provides oxygenated blood to either or both of the coronary arteries by means of a small plastic tubing attached to a coronary perfusion cannula which fits into the coronary ostia (openings) within the aortic root. In such coronary perfusion, as well as systemic perfusion, a pulsatile flow has been desired but has heretofore been unattainable. This problem is also solved by a smaller embodiment of the apparatus of the present invention, provided for insertion into the coronary perfusion line between the roller pump and coronary perfusion cannula to provide pulsatile perfusion to the coronary arteries.

Many other applications of the present invention are possible, all as more fully explained hereinafter in connection with the accompanying drawings where:

DESCRIPTION OF THE INVENTION

Figure 2:
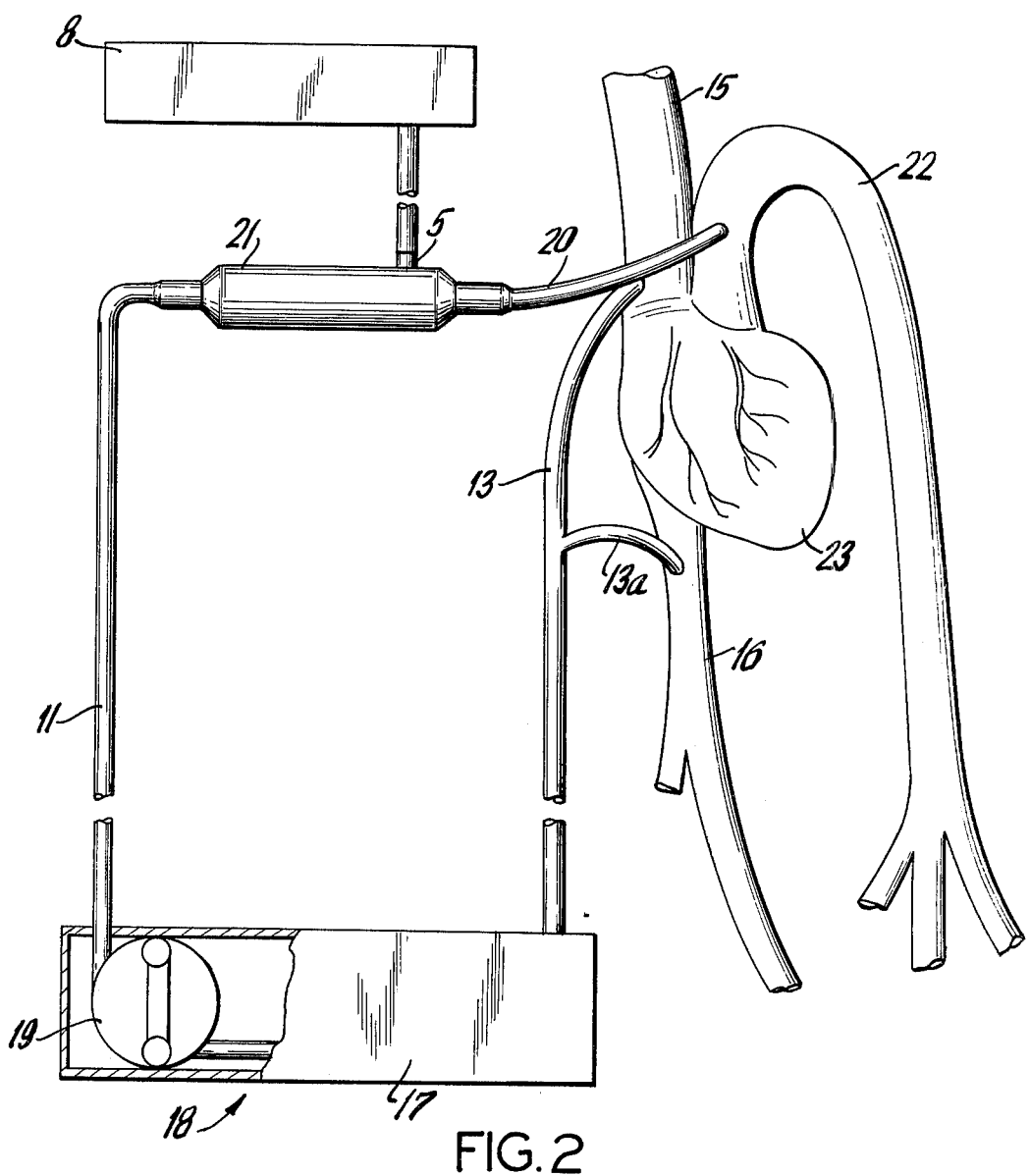
FIG. 2 is a schematic diagram of heart-lung circuitry equipped to provide pulsatile flow in accordance with the present invention.

Typical heart-lung circuitry as used in most types of heart surgery is illustrated in FIG. 2. The heart 23, due to illness, or because damaged in some other manner, is not capable of maintaining the pumping action necessary to maintain life. Accordingly, what is generally referred to as a heart-lung machine is connected to the patient to either take over from, or to assist the heart in its blood pumping function while the heart is being repaired. The heart-lung machine basically consists of two elements, a pumping portion to pump the blood, and an oxygenator to supply the blood with oxygen since during this type of surgery the lungs usually cannot adequately perform that function.

In FIG. 2, the heart-lung machine is shown schematically at 18. It consists of an oxygenator portion 17 and a pump portion 19. In present day heart-lung machines occlusive roller pumps are generally used as the pumping section. Actual pumping is achieved by the action of one or more rollers within the head of a pump, against a section of soft plastic tubing circumferentially disposed against the inner wall of the pump housing. The rollers, rotating in a circular motion, squeeze the blood contained in the plastic tubing in a direction coincidental to their direction of rotation. Blood is therefore delivered under pressure from the pump tubing in a constant, non-pulsatile flow. Flow rates can be varied by varying the roller pump r.p.m.

The roller pump 19 pumps the blood in a non-pulsatile manner through tubing 11. In a conventional heart-lung machine, device 21 (to be described below) is not present and thus the blood passes through tubing 11 and cannula 20 into the aorta 22, cannula 20 having been surgically inserted therein. The action of pump 19 causes the blood to flow through aorta 22 to all parts of the body's arterial system, where it gives up its oxygen and then returns via the body's venous system. Cannulae 13 and 13a are surgically inserted into the main veins of the body, the superior vena cava 15 and the inferior vena cava 16, respectively, and the blood flowing in these veins is returned through cannulae 13 and 13a to the oxygenator portion 17 of the heart-lung apparatus 18, where it picks up fresh oxygen, reenters the pump 19, and is recirculated to the body by pump 19 as described above.

It can be seen that the flow of blood provided is non-pulsatile, simply being provided in a steady stream by roller pump 19. Also since roller pump 19 operates by squeezing the tubing containing the blood, the blood undergoes considerable trauma due to this squeezing action. It is an object of the present invention to convert this steady blood flow into a pulsatile blood flow, yet to do so without introducing any additional trauma to the blood.

The condition of the blood is a critical factor in determining the length of time which the patient can be connected to a heart-lung machine and hence the length of time available to operate on and repair a damaged heart. Thus, the less trauma the blood is subjected to the more time available for surgery and the better the patient's chances. On the other hand, it has been found that the patient's organs and overall body functions perform better when the blood flow is pulsatile, simulating that provided naturally by the heart.

Figure 1:
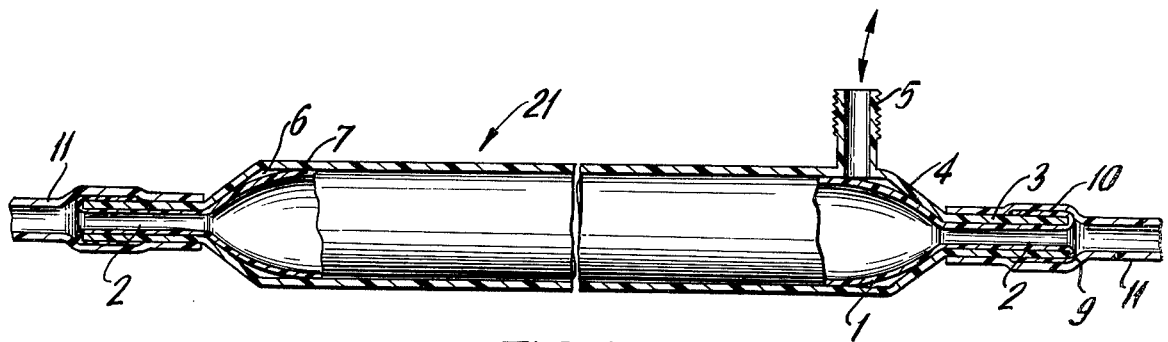
FIG. 1 is a sectional view of the preferred embodiment of the pulsatile pumping apparatus of the present invention.

The present invention meets both these needs by providing additional pulsatile pumping of the blood, but doing so with little or no increased trauma and in a manner which requires no additional surgery. This is accomplished by inserting device 21 in series with roller-pump 19 as shown in FIG. 2. Apparatus 21 is illustrated in FIG. 1. A double-ended balloon-like member is fabricated from a biologically compatible flexible plastic to form an extremely thin, smooth, easily collapsible tubular member 1. Both necks 2 of this member extend into and through the narrowed ends 3 of a rigid housing 4 constructed of an appropriate transparent plastic. The necks 2 are everted over the rounded ends 9 of the housing ends 3. The everted ends 10 are then bonded to the exteriors of ends 3. Fixed lengths of plastic tubing 11 of the sort used in heart-lung machine circuitry are then slipped over the ends of the housing, over which the tubular member ends have been everted and sealed. The plastic tubing may now be bonded to the everted tubular member ends 10 and the housing ends 3 forming a pressure-tight seal at that point. It can be clearly seen by this description that the blood flowing through this apparatus comes into contact with no surface other than that of the smooth unbroken surface of the tubular member until it passes into the heart-lung tubing. An air fitting 5, which may be threaded, is incorporated into the rigid housing and penetrates into the space 6 between the tubular member 1 and the inner wall 7 of the housing. When space 6 is filled with compressed gas the tubular member 1 assumes a new collapsed geometry thereby ejecting the blood contained in the tubular member from both ends. Compressed air or other suitable gas is supplied to apparatus 21 by a suitable driving source 8. Pneumatic pressures, vacuum, durations, delays and filling times are controlled and regulated by this driving source to deliver a pneumatic pressure to apparatus 21 via the air fitting 5 to collapse the blood containing tubular member 1, thereby ejecting the contained blood in a predetermined rhythm of pulsation. This strong ejection of blood is timed to the patient's physiological needs by either his ECG or a pressure pulse from a pulsatile pressure wave in the patient's circulatory system through this conventional control unit. Ejected blood then flows through the aortic cannula 20 into the ascending aorta 22 in a pulsatile flow that mimicks the waveform delivered by the natural heart 23 when it is functioning. The intrinsic occlusive action of the roller pump 19 serves as a check valve to prevent ejected blood from moving retrograde into the pump line rather than directly ahead into the aortic cannula 20, thereby eliminating the need for other valves which would traumatize the blood. The suitable driving source 8 alternately delivers vacuum to the air space 6 of apparatus 21 in a controlled manner, thus forcing the tubular member 1 to resume its natural geometry allowing it to fill from the roller pump output.

Figure 3:
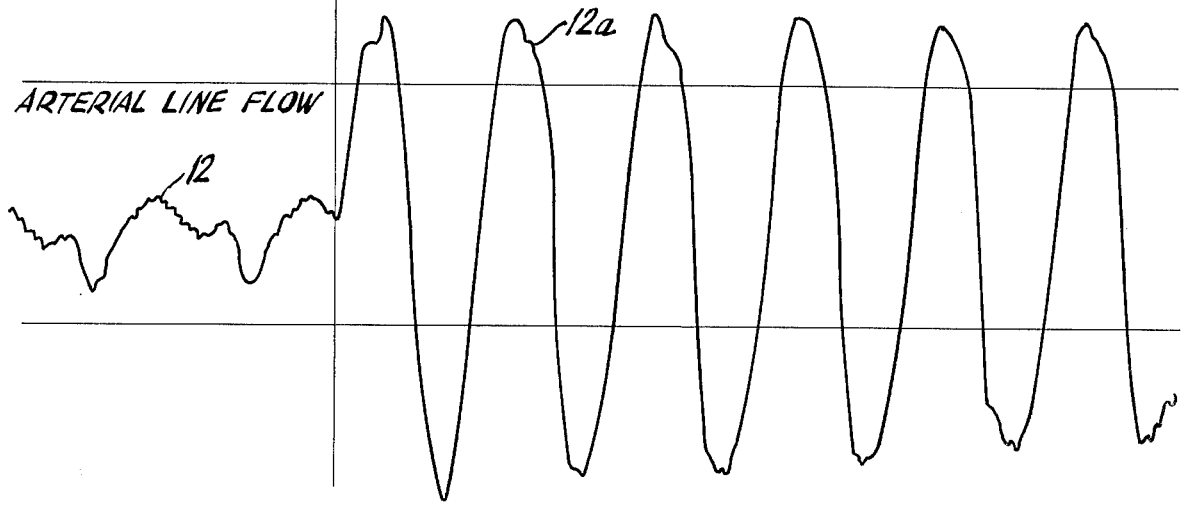
FIG. 3 is a plot of the blood flow both before and after being provided with the pulsatile flow of the present invention.

Thus, it can be easily seen that the insertion of device 21, and its associated control unit 8, into the heart-lung circuitry in series with roller pump 19 converts the normally non-pulsatile flow of pump 19 into a pulsatile flow, yet does so without further traumatizing the blood and without the need for additional surgery on the patient. The extent of the pulsatile flow created is illustrated by the plots of FIG. 3 where the part of the plot designated as 12 shows the blood flow pattern with only the roller pump and the part of the plot designated as 12a shows the blood flow pattern when apparatus 21 is added in series with roller pump 19. It is apparent from FIG. 3 that the blood flow is relatively flat when pumped only by roller pump 19 but is highly pulsatile when also subjected to apparatus 21.

The apparatus of the present invention has the additional advantage of being able to function as a counterpulsation device. Counterpulsation can be defined as the process of withdrawing or receiving blood from the left ventricle during systole and injecting or replacing blood into the aorta during diastole. It is preferred that withdrawal and replacement take place directly above the aortic valve; that the receiving reservoir offer no resistance to the inflow of blood; that injection begin as soon as outward ventricular flow stops (slightly before the valve closes); and that the force of injection produce the same impulsive pressure as would have been produced in normal systole. Counterpulsation thus defined has two distinct phases or intervals. And it is most important to note that the circulatory system is assisted in each of these phases.

The ventricular muscle must do work because the aortic tree offers resistance to the inflow of blood, and the ventricle must maintain continuous pressure throughout the ejection period. By providing a temporary reservoir for ejected blood, ideal counterpulsation prevents the ventricle from seeing the aortic resistance, and ejection takes place with less force required. During the diastolic phase, the counterpulsation source pumps into the normal arterial tree against resistance, and so does the work. Whatever work no longer demanded of the heart is therefore provided instead by the counterpulsation power source.

The present invention can function to provide this counterpulsation in the following manner. Often when a patient is to undergo heart surgery it is helpful to provide counter-pulsation to help the sick heart for a period before the full aid of the heart-lung apparatus is to be utilized. Similarly, after the operation, it is very helpful to provide the patient with counterpulsation in order to help take him off the heart-lung machine. In both cases, the weak heart is assisted by counterpulsation in order to make it function as easily as possible. Referring to FIG. 2 it will be seen that counter-pulsation can be accomplished by merely stopping the roller pump 19 and utilizing the device 21 as a counterpulsation device. While it is the general practice when stopping the roller pump to place a tubing clamp on tubing 11, if the pump operator elects not to place the clamp, but merely stops the pump, the occlusive action of the roller pump itself will serve to act as a valve or clamp which will enable device 21 to function as a counterpulsation device. In this counterpulsation mode, the driving unit 8 is operated and is controlled either by the patient's ECG or another appropriate input signal, to collapse and reopen the tubular member in a rhythm synchronous to that of the left ventricle systole. The apparatus 21 is signaled by the aforementioned control means 8 to eject a fixed bolus of blood into the ascending aorta immediately after the aortic valve has closed, indicating the end of cardiac systole. This additional bolus of blood delivered under a pressure higher than that which the impaired left ventricle is capable of delivering by itself aids in the perfusion of the systemic circulation as well as that of the coronary arteries. Immediately to the next cardiac systole the driving unit provides a vacuum in the space 6 of apparatus 21 thus rapidly returning the inflatable member 1 to its uncollapsed state. This action sucks a bolus of blood from the ascending aorta into apparatus 21 and reduces the end diastolic pressure in the aorta, thus enabling the ventricle to eject its own bolus of blood into an area of reduced pressure thereby saving it pressure work and oxygen consumption and generally adding to its well being. Another benefit of the present invention is to assist in weaning the patient off the heart-lung machine by means of the aforementioned counterpulsation. It has been extremely difficult in the past, on many occasions, for the patient's own heart to assume its pumping duties after having been taken over by the heart-lung machine. On those occasions weaning away from the machine may require a length of time which may further traumatize the blood. In those cases where the patient's heart cannot deliver life supporting blood pressures after surgery, the surgeon may elect to provide counterpulsation as described above until the heart recovers enough to maintain acceptable blood pressures, thus reducing the time the patient must be on the heart-lung machine and therefore reducing the trauma to the blood. Assistance to the heart by this counterpulsation method may be supplied to every beat at the first and then by adjusting the driving unit 8 to assist every other beat and finally every third beat, thus gradually bringing the heart back to normal operation at which point the counterpulsation is stopped entirely and the heart resumes full load. The surgeon may also eject by operating the controls on the driving source 8 to increase or decrease or to regulate the magnitude of the pulsatile excursion. Such controlled excursion may further enhance the weaning away of the patient from cardiopulmonary bypass support. In addition, blood in increments may be returned to the patient while cardiopulmonary bypass is in progress without stopping the device.

Figure 4:
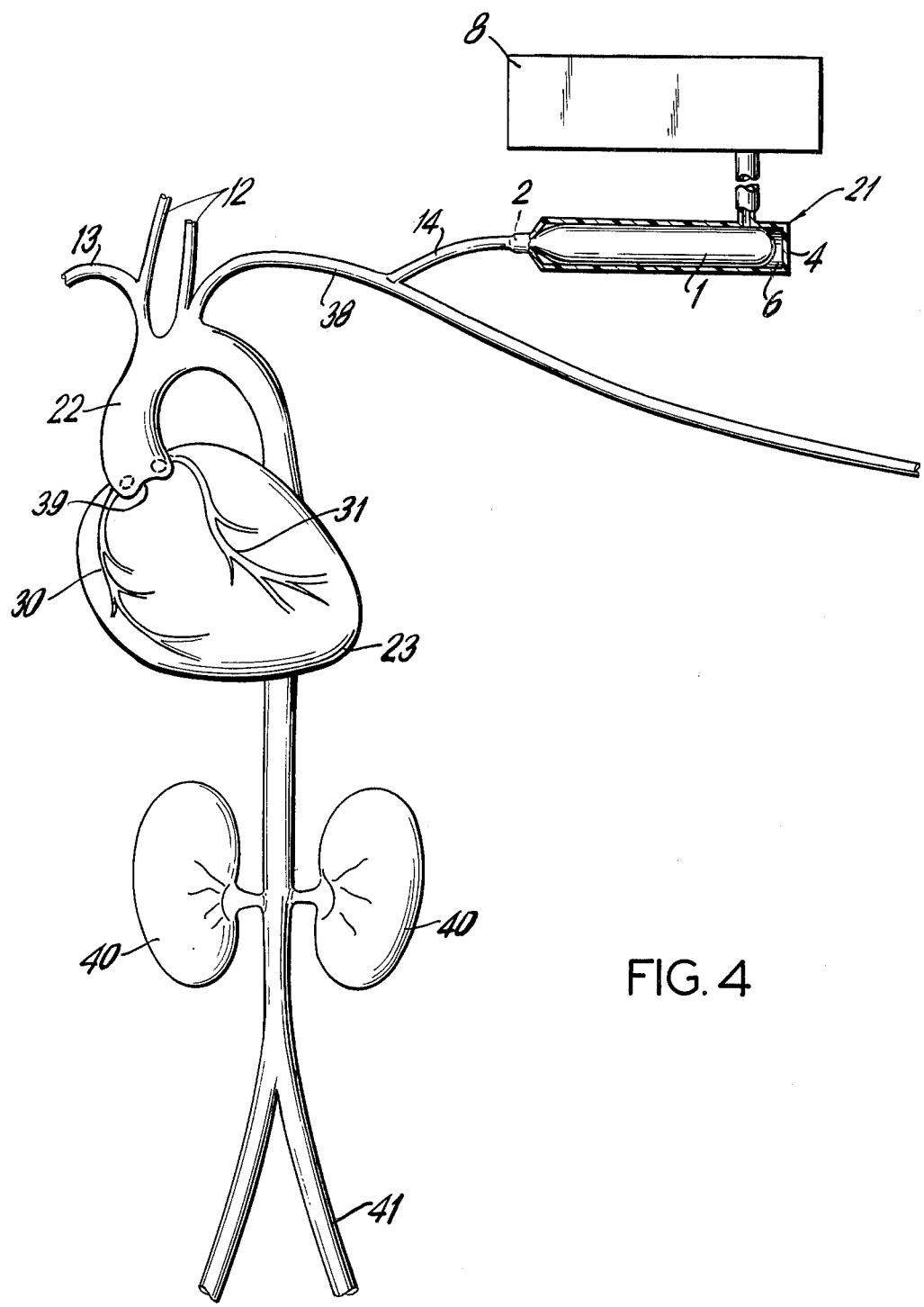
FIG. 4 is a schematic diagram of a method of using a modification of the pulsatile flow device as a counterpulsation device.

In some situations it may be desirable to counter-pulsate the heart where the patient is not otherwise being subjected to surgery. Such situations can arise anytime the heart is weakened but not weakened enough to require radical open heart surgery. In such cases it is desirable to counter-pulsate the heart in order to reduce its workload but with a minimum of surgery on the patient. The present invention can also accomplish this purpose as illustrated in FIG. 4.

It will be seen that the tubular member 1 disposed within the rigid housing 4 is sack-like in that it has only one neck 2. A cannula 14 enters the left auxillary artery 38 at a point close to the aortic arch 22. However, the cannula can be inserted at any point through any convenient artery, such as the femoral artery, the configuration shown being only illustrative. A signal from the patient's ECG or from some other suitable signal, such as the patient's pressure pulse, enters the control system 8 to indicate closure of the aortic valve 39. Air or a suitable gas under pressure is allowed to enter air space 6 of the present invention collapsing the tubular member 1. Blood is thus ejected from the tubular member into the auxillary artery and into the aortic arch 22 via the cannula 14 and artery 38. In addition to augmenting the pressures and flows (perfusion) of the systemic circulations (e.g., left auxillary 38, renals 40, femorals 41, etc.) this bolus of blood, under increased pressure, perfuses the coronary arteries 30, 31 since they can only be perfused during heart diastole. Immediately prior to heart systole the control system 8 allows vacuum to evacuate the air space 6 rapidly so that rapid filling of tubular member 1 takes place. A bolus of blood equal to or nearly equal to the volume of the tubular member is then rapidly withdrawn from the aorta 22 lowering the pressure in the aorta and saving work for the ventricle thus lowering its oxygen consumption.

Since the inflatable member does not have to be inserted into the artery as in the present day intra-aortic balloon pumping, the present invention can be used in various sites close to the aortic arch whenever a cannula of sufficient size to handle the blood can be inserted. It can also be used where the insertion of an intra-aortic balloon pump is surgically impossible, since all that need enter the patient is cannula 14. Thus, in the configuration the present invention provides pulsatile counterpulsation with a minimum of surgery to the patient.

Figure 5:
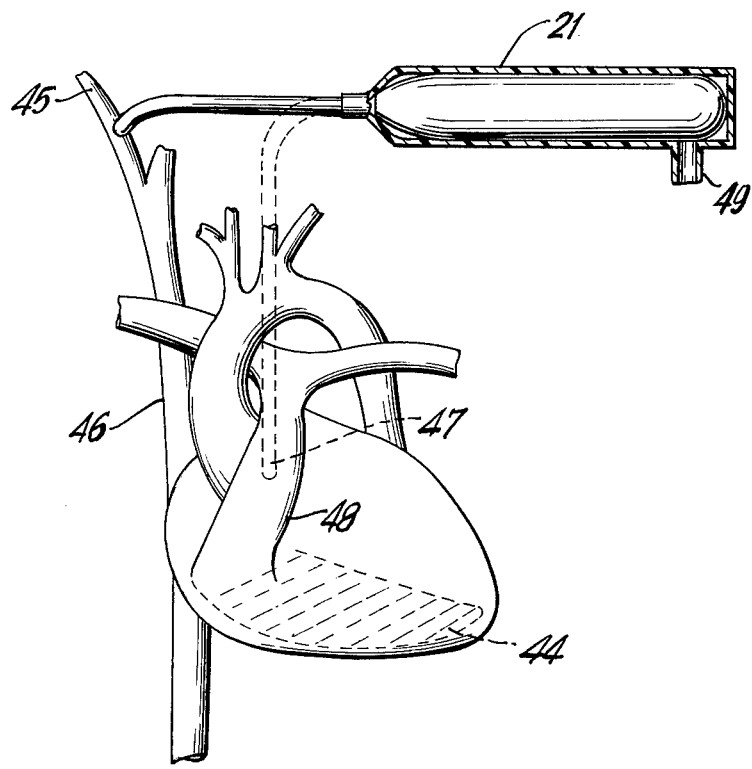
FIG. 5 is a schematic diagram of another method of using a modification of the pulsatile flow device as a counterpulsation device.

The present invention can be used in this single-ended counterpulsation mode to provide any desired type of counterpulsation. For example, FIG. 5 illustrates the use of the single-ended embodiment of the present invention to counter-pulse the pulmonary artery to assist a failing right heart. As in left heart counterpulsation, an ECG signal from the patient, or some other suitable signal, allows the device to inject or withdraw a bolus of blood from the pulmonary artery in counter-pulsation synchronous with the contractions of the right ventricle. This is accomplished, as heretofore by air/vacuum 49 from a suitable control unit. The lowering of pulmonary artery pressure and increased perfusion through the lungs can then be accomplished in a manner analogous to left ventricle counter-pulsation. As seen in FIG. 5, the pulmonary artery 48 can be reached either by cannulation of the external jugular vein 45, or via the internal jugular vein, superior vena cava 46, to the right atrium and to the right ventricle; or a cannula 47 can be inserted directly into the pulmonary artery 48 should that vessel be available, or even via cannulation of the femoral vein to the vena cava.

In addition to doing the work of the heart by providing the heart-lung machine with non-traumatic pulsatile flow and to aiding the heart by providing non-traumatic pulsatile counter-pulsation, the present invention can also be used to provide non-traumatic pulsatile blood flow to the heart itself.

Figures 6, 7:
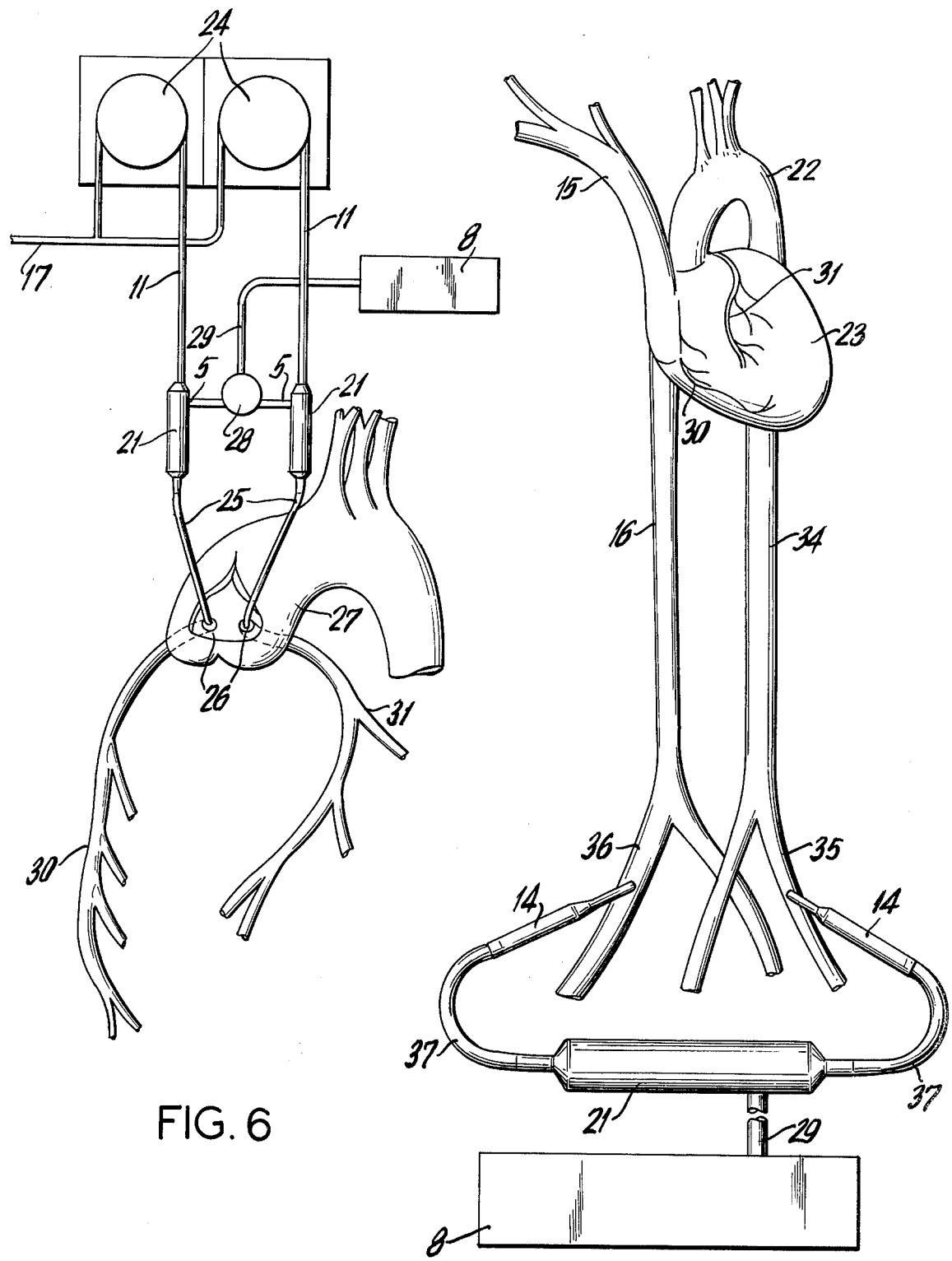
FIG. 6 is a schematic diagram of heart-lung circuitry equipped to provide pulsatile coronary perfusion in accordance with the present invention.
FIG. 7 is a schematic diagram of a method of assisting the pumping of the heart with pulsatile flow in a situation where the condition of the patient does not require full heart-lung circuitry.

During certain operative procedures, it is necessary to cross clamp the aorta at some point between the arterial cannula 20 (FIG. 2) and the heart 23 (FIG. 2) for extended periods thereby denying the support of the heart-lung machine to the heart's own (coronary) arteries. At this time the surgeon may elect to perfuse the coronary arteries by inserting small cannulae into the openings (ostia) of these arteries within the root of the aorta. Small roller pumps are provided in the heart-lung machine for this function. The object of this aspect of the present invention is to convert the non-pulsatile nature of the flow of the coronary perfusion pumps into a pulsatile flow. Referring to FIG. 6, it will be seen that smaller embodiments of apparatus 21 are inserted into the arterial pressure lines 11 between the coronary perfusion pumps 24 and the coronary perfusion cannulae 25. These cannulae are shown in place (out of scale) in the coronary ostia 26 in the opened aortic root 27.

Oxygenated blood enters the perfusion pumps 24 via a line from the oxygenator 17. It is then delivered as a steady flow to apparatus 21. These pulsatile devices 21 convert the non-pulsatile input to a pulsatile output in response to the pressure/vacuum delivered by the driving source 8 in the same manner as apparatus 21 described in connection with FIG. 2. The driving source 8 may be triggered by the patient's ECG or some other suitable triggering means. Pneumatic pressure/vacuum is directed to either the right or left device, or to both, or to neither by the action of a four-way manually operated valve 28. As will be seen, this valve lies between the device air inlets 5 and the driving source air output line 29. The right and left coronary arteries 30, 31 thus are perfused by a non-traumatic pulsatile flow.

The present invention can also serve as a synchronous pulsating arterio-venous fistula as illustrated in FIG. 7. In this mode, apparatus 21 serves as a low resistance conduit in ventricular systole acting as a phasic runoff, thus decreasing heart afterload without decreasing coronary perfusion. The ends of the device 21 are inserted by cannula 14 into a vein 36 and an artery 35 of the systemic peripheral circulation. The vein and artery illustrated are the femorals but the invention is not limited to the exclusive use of these two arteries and veins. Appropriate tubing 37 and cannula are employed to achieve circuitry. Closing of the aortic valve indicates an end of systole to the driving unit 8 via the patient's ECG or other suitable means. The driving unit 8 then triggers a release of air into the air space of apparatus 21 collapsing the tubular member and ejecting blood omnidirectionally into the venous and arterial systems. This ejection preserves the systemic diastolic pressure and increases coronary perfusion which takes place only during ventricular diastole. At the end of cardiac diastole, the driving unit 8 is again signaled to allow vacuum to enter air line 29 and the tubular member is thus allowed to relax into an uncollapsed state, once again, serving as a low resistance conduit to the blood ejected by the impaired ventricle. This use of the present invention is not limited to the operating room. It may be used medically as an adjunct treatment to an acutely impaired heart following a myocardial infarct, ventricular aneurysm, etc.

We claim:
1. Apparatus for providing a pulsatile flow of blood to a patient or an organ comprising:
    a. an avalvular elongated rigid housing having openings at both ends;
    b. an avalvular double open-ended elongated collapsible essentially impermeable thin-walled balloon-like member disposed within said housing, the diameter of said balloon increasing inwardly from the open ends, the ends of said balloon-like member sealed to the opened ends of said housing;
    c. a port opening into said housing at a point other than at its opened ends;

d. control means communicating with said port to deliver and remove a control medium to and from said housing to alternately collapse and cause said thin-walled balloon-like member to inflate in dependence on patient's or organ's physiologic needs; and e. pump means coupled to receive blood from a patient at its input to provide a substantially steady flow of blood at its output; and f. avalvular means coupling the output of said pump to one end of said avalvular elongated rigid housing, the output of said pulsatile means thereby being adapted to terminate in a cannula to supply blood to a patient.

2. Apparatus according to claim 1 wherein said port comprises a single port and wherein said control means are adapted to deliver a control medium alternately under a pressure and a vacuum to cause said balloon-like member to collapse and eject blood when the control medium enters said housing and to expand and fill with blood when the control medium is drawn out of said housing under a vacuum.

3. The apparatus of claim 2 wherein said control medium is a gas.

4. The apparatus of claim 1 wherein said control medium is a gas.

5. Heart-lung apparatus for providing a pulsatile flow of oxygenated blood to a patient or an organ comprising:

a. pump means to provide at its output a substantiatilly steady flow of oxygenated blood;

b. avalvular pulsatile means comprising:
1. an avalvular elongated rigid housing having openings at both ends;
2. an avalvular double open-ended elongated collapsible essentially impermeable thin-walled balloon-like member disposed within said housing, the diameter of said balloon increasing inwardly from the open ends, the ends of said balloon-like member sealed to the opened ends of said housing;
3. a port opening into said housing at a point other than at its opened ends;
4. control means communicating with said port to deliver and remove a control medium to and from said housing to alternately collapse and cause said thin-walled balloon-liked member to inflate in dependence on the patient's or organ's physiologic needs; and c. avalvular means connecting said pump means and said pulsatile means;

d. avalvular conduit means coupled to the output of said pulsatile means for delivery of said control pulsatile flow to the patient;

e. means for conducting said blood from the patient;

f. means having an input coupled to said conducting means for oxygenating the blood removed from the patient and providing oxygenated blood at its output; and g. means coupled to the output of said oxygenating means for conducting said oxygenated blood to the input of said pump means.

6. The apparatus of claim 5 wherein said avalvular connecting means comprise a first tubular member coupled to the end of said balloon-like member at the open end of said housing proximate to said pump means and wherein said conduit means comprise a second tubular member force fitted over the end of said balloon-like member on the open end of said housing distal from said pump means, said second tubular member terminating in a cannula for insertion into the patient.

7. Apparatus according to claim 5 wherein said port comprises a single port and wherein said control means are adapted to deliver medium alternately under a pressure and a vacuum to cause said balloon-like member to collapse and eject blood when the control medium enters said housing and to expand and fill with blood when the control medium is drawn out of said housing under a vacuum.

8. The apparatus of claim 7 wherein said control medium is a gas.

9. Apparatus for providing a pulsatile flow of blood to a patient or an organ comprising:

a. an avalvular elongated rigid housing having openings at both ends;

b. an avalvular double open-ended elongated collapsible essentially impermeable thin-walled balloon-like member disposed within said housing, the diameter of said balloon increasing inwardly from the open ends, the ends of said balloon-like member sealed to the opened ends of said housings;

c. a port opening into said housing at a point other than at its opened ends;

d. control means communicating with said port to deliver and remove a control medium to and from said housing to alternately collapse and cause said thin-walled balloon-like member to inflate in dependence on the patient's or organ's physiologic needs; and e. a first tubular member coupled to one end of said balloon-like member at one open end of said housing and terminating in a cannula to be inserted into the blood circulatory system of the patient's body.

10. Apparatus according to claim 9 wherein said first cannula comprises an arterial cannula and further including a second tubular member coupled to the other end of said balloon-like member at the other end of said housing adapted to be coupled to receive a supply of blood.

11. The apparatus of claim 9 wherein said first cannula is an arterial cannula and further including a second tubular member coupled to the other end of said balloon-like member at the other open end of said housing and means for sealing on the end of said second tubular member to prevent any flow of blood through said second tubular member.

12. Pulsating aterio-venous fistula apparatus comprising:

a. an avalvular elongated rigid housing having openings at both ends;

b. an avalvular double open-ended elongated collapsible essentially impermable thin-walled balloon-like member disposed within said housing, the diameter of said balloon increasing inwardly from the open ends, the ends of said balloon-like member sealed to the opened ends of said housing;

c. an avalvular first tubular member coupled to one end of said balloon-like member at one open end of said housing and terminating in an arterial cannula;

d. an avalvular second tubular member coupled to the other end of said balloon-like member at the other open end of said housing and terminating in a venous cannula;

e. a port opening into said housing at a point other than at its open ends; and f. control means communicating with said port to deliver and remove a control medium to and from said housing to alternately collapse and cause said thin-walled balloon-like member to inflate in dependence on the patient's or organ's physiologic needs.

13. Apparatus for providing a pulsatile flow of blood to the coronary arteries of the heart comprising:
   a. pump means, having an input adapted to be coupled to receive blood from a patient, to provide, at at least two outputs, a substantially steady flow of blood;
   b. at least first and second avalvular pulsatile means having their inputs respectively coupled to said at least two pump outputs to convert said steady flow to pulsatile flow at their outputs without causing additional trauma to the blood, said outputs adapted to to be connected to the coronary arteries of the heart;
   c. control means to deliver a control medium to each of said pulsatile means in order to control the nature of said pulsatile flow; and
   d. valve means connected to said control means and to each of said pulsatile means to direct the flow of said control medium to each of said pulsatile means.

14. The apparatus of claim 13 wherein each of said pulsatile means comprises:
   a. an avalvular elongated rigid housing having openings at both ends;
   b. an avalvular double open-ended elongated collapsible balloon-like member disposed within said housing, the ends of said balloon-like member being everted over the open ends of said housing; and
   c. a port communicating with said valve means and opening into said housing at a point other than at its open ends to permit the control medium to enter and leave said housing.

15. The apparatus of claim 14 wherein said control medium is a gas and wherein said valve means directs said gas to either, both or neither of said pulsatile means in order to cause either, both or neither of said balloon members to collapse and eject blood when the gas enters said housings or to expand and fill with blood when the gas leaves said housings.

* * * * *

UNITED STATES PATENT AND TRADEMARK OFFICE
CERTIFICATE OF CORRECTION

PATENT NO. : 4,080,958
DATED : March 28, 1978
INVENTOR(S) : Bregman, David; Hanson, Bruce L.; Wolvek, Sidney It is certified that error appears in the above-identified patent and that said Letters Patent are hereby corrected as shown below:

Col., 6, line 17 - between "Immediately" and "to" insert "prior"

Col. 6, line 42 - delete "the"

Col. 6, line 47 - change "eject" to "elect"

Col. 6, line 67 - change "auxillary" to "axillary"

Col. 7, line 10 - change "auxillary" to "axillary"

Col. 7, line 13 - change "auxillary" to "axillary"

Col. 7, line 25 - delete "the", second occurrence.

Col. 10, line 6 - between "deliver" and "medium" insert "a control"

Signed and Sealed this

Eighteenth Day of July 1978

[SEAL]

Attest:

RUTH C. MASON
*Attesting Officer*

DONALD W. BANNER
*Commissioner of Patents and Trademarks*